United States Patent [19]

Price et al.

[11] Patent Number: 5,705,191
[45] Date of Patent: Jan. 6, 1998

[54] SUSTAINED DELIVERY OF ACTIVE COMPOUNDS FROM TUBULES, WITH RATIONAL CONTROL

[75] Inventors: Ronald R. Price, Stevensville, Md.; Joel M. Schnur, Burke, Va.; Alan S. Rudolph, Potomac; Jonathan Selinger, Silver Spring, both of Md.; Alok Singh, Springfield, Va.; Bruce P. Gaber, Bethesda, Md.

[73] Assignee: The United States of America as represented by the Secretary of the Navy, Washington, D.C.

[21] Appl. No.: 523,725

[22] Filed: Aug. 18, 1995

[51] Int. Cl.⁶ .................................................. A61K 9/24
[52] U.S. Cl. ........................ 424/473; 424/450; 604/890.1
[58] Field of Search .............................. 424/473, 450; 604/890.1

[56] References Cited

U.S. PATENT DOCUMENTS

| | | | |
|---|---|---|---|
| 4,017,303 | 4/1977 | Koester | 75/0.5 AA |
| 4,720,384 | 1/1988 | DiLuccio | 424/78 |
| 4,867,917 | 9/1989 | Schnur | 260/413 |
| 5,049,382 | 9/1991 | Price | 424/450 |
| 5,290,960 | 3/1994 | Singh | 554/79 |
| 5,366,881 | 11/1994 | Singh | 435/177 |
| 5,492,696 | 2/1996 | Price | 424/417 |

*Primary Examiner*—D. Gabrielle Phelan
*Attorney, Agent, or Firm*—Thomas E. McDonnell; John J. Karasek

[57] ABSTRACT

The present invention is a method for releasing an active agent into a use environment, by disposing this active agent within the lumen of a population of tubules, and disposing the tubules into a use environment, either directly or in some matrix such as a paint in contact with the use environment. The tubules have a preselected release profile to provide a preselected release rate curve. The preselected release profile may be achieved by controlling the length or length distribution of the tubules, or by placing degradable endcaps over some or all of the tubules in the population, or by combinations of these methods. The invention is also a population of tubules having a preselected release profile to provide a preselected release rate curve.

9 Claims, 9 Drawing Sheets

SUSTAINED DELIVERY OF ACTIVE COMPOUNDS FROM TUBULES, WITH RATIONAL CONTROL

BACKGROUND OF THE INVENTION

1. Field of the Invention

This invention relates to the controlled release of active agents from tubules, and more particularly to the controlled release of active agents from tubules with rational control, through the use of tubules with preselected lengths or length distributions, and through the use of degradable tubule endcaps of selected thickness.

2. Description of the Related Art

Active agents are chemicals that have some effect in some environment of use. For almost any active agent, for use in almost any use environment, it is desired to modulate the release of the active agent into the use environment, so that the active agent is released into the use environment at a selected rate, and over a selected time. There are several, frequently complementary, reasons for modulating active agent release.

Many active agents are preferably released at a desired concentration, or in a desired concentration range. Drugs, for example, are preferably introduced into the body within a therapeutic range. Below this range, there will not be enough of the drug in the body to achieve the desired therapeutic effect. Above this range, no additional therapeutic effect will be conferred, or adverse side effects of the drug will outweigh the therapeutic effect of the drug.

Analogous dynamics are at work for most every active agent. As another example, antifouling agents for use on ship hulls are typically environmentally unfriendly. Thus, it is desired to control the release rate of these antifouling agents, to keep their release into the environment at an acceptable level. At the same time, it is desired to release these antifouling agents at effective levels. See generally U.S. Pat. No. 5,049,382, issued Sep. 17, 1991 to Price et al, incorporated by reference herein, in its entirety, for all purposes.

Likewise, many active agents are preferably released at a sustained rate over a desirable period. For example, many drugs (e.g., antibiotics) are preferably absorbed and metabolized by the body over a prolonged therapeutic course of treatment. Traditionally, this is done by administering repeated, regular doses (e.g., regular oral or injected doses), or by a sustained administration, such as an intravenous drip. Other drugs (e.g., antihypertensive drugs, birth control hormones) do not have a finite course of treatment. For these drugs, sustained controlled delivery is a matter of convenience and an assurance against a lapse of memory.

Sustained delivery is also desired for many other active agents. For antifouling agents, it is highly desirable to sustain delivery of an effective amount of the antifouling agent for as long as possible, to maximize the time between applications of the agent. For pesticides, pheromones, and other active agents used to control pest populations, sustained delivery of these agents for at least the duration of a growth or reproduction cycle is highly desirable. See generally U.S. Pat. No. 4,017,303, issued Apr. 12, 1977 to Coplan et al, incorporated by reference herein, in its entirety, for all purposes.

Tubules, especially lipid tubules, are known to be useful for encapsulation and release applications. See, e.g., U.S. Pat. Nos. 5,366,881 and 4,867,917, incorporated by reference herein, in their entireties, for all purposes.

One shortcoming of existing tubule-based release applications has been the difficulty in achieving the desired predictability and control over the release rate. For example, the relationship between tubule properties and release rates has not been characterized.

Another shortcoming of existing tubule-based release applications has been that all the tubules in a given system follow roughly the same release profile. The result of this is that when one tubule in a system runs out of active agent, all the tubules in the system run out of active agent at about the same time, and that the fraction of active agent that is usefully released (within the range of desired target release rates) is sub-optimal.

Another shortcoming of existing tubule release systems has been that many tubule-based release systems permit the tubules to begin releasing active agent immediately upon encapsulation, without regard to whether the tubules have been exposed to the use environment.

SUMMARY OF THE INVENTION

Accordingly, it is an object of this invention to use tubules, including lipid tubules, in a delivery system with rational control of the release profile.

It is a further object of this invention to use tubules in a delivery system with selected fractions of the tubules in the system following different preselected release profiles.

It is a further object of this invention to provide a tubule-based delivery system where all or selected fractions of the tubules in the delivery system begin to release active agent when exposed to the use environment, either shortly after exposure or after a selected delay period.

These and additional objects of the invention are accomplished by the structures and processes hereinafter described.

The present invention is a method for releasing an active agent into a use environment, by disposing this active agent within the lumen of a population of tubules, and disposing the tubules into a use environment, either directly or in some matrix such as a paint in contact with the use environment. The tubules have a preselected release profile to provide a preselected release rate curve. The preselected release profile may be achieved by controlling the length or length distribution of the tubules, or by placing degradable endcaps over some or all of the tubules in the population, or by combinations of these methods. The invention is also a population of tubules having a preselected release profile to provide a preselected release rate curve.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DETAILED DESCRIPTION OF THE PREFERRED EMBODIMENTS

The Effect of Tubule Length Distributions on Release Rate

For some types of tubules, is will be possible to prepare monodisperse or nearly monodisperse populations, i.e., populations where the tubules are the same length or nearly the same length. For example, metallized tubules or other sturdy tubules (e.g., ceramic or inorganic tubules such as the minerals halloysite, cylindrite, and boulangerite) may be filtered or centrifuged to achieve a narrow length distribution. Likewise, metallic tubules may be grown in membranes to a uniform length. This may be accomplished by utilization of a polycarbonate membrane of a known and desired thickness, which has pores normal to the surface of the membrane and penetrating through the thickness of the membrane. The membrane is activated by floating it on a solution of the catalyst which then reacts with one surface and is pulled into the lumen of the pores by capillary attraction, thus covering catalyst on the walls of the central tubular pores. The membrane is then rinsed to remove the excess catalytic material and then is once again floated on the surface of the electroless plating bath which then only reacts with the catalyzed inner surface of the pores and not the uncatalyzed outer surface of the membrane, the reacted side being opposite the bath.

However, it has been determined experimentally and through modelling that lipid tubule populations (where the tubules are relatively fragile and prone to breakage over time) tend to a population distribution described by $$\rho(L) = \frac{1}{L_0} \exp\left(-\frac{L}{L_0}\right)$$

where $L_0$ is the mean length and $\rho(L)$ is the population distribution as a function of tubule length. Considering an infinitesimal length $dL$ along a tubule, where the probability of a break in that region is $dL/L_0$, the probability that there is no break in that region is $1-dL/L_0$. To find the probability that there is no break in a finite length L, it may be divided into n shorter, equal lengths $dL=L/n$. The probability that there is no break is then $(1-dL/L_0)^n=(1-L/nL_0)^n$. At the limit $n \to \infty$, this probability becomes $\exp(-L/L_0)$. The probability that a tubule has a length between L and L+dL is the probability that it has a length L with no break multiplied by the probability that it has a break between L and L+dL, which is $(dL/L_0) \exp(-L/L_0)$. Therefore, it is predicted that the distribution of microcylinder lengths should be as given above. Experimental confirmation of this distribution has been obtained (see below).

It has been determined that the release of an active agent from a tubule may be described by the effective one-dimensional diffusion equation $$\frac{\partial c(x,t)}{\partial t} = D \frac{\partial^2 c(x,t)}{\partial x^2}$$

where c(x,t) is the concentration of the active agent at position x and time t, and D is the effective one-dimensional diffusion constant.

It has been determined that the release rate from a monodisperse (i.e., essentially equal length) population of tubules may be given as:

$$c(x,t) = \sum_{n=0}^{\infty} \frac{4c_0}{(2n+1)\pi} \exp\left(-\frac{(2n+1)^2\pi^2 Dt}{L^2}\right) \sin\left(\frac{(2n+1)\pi x}{L}\right)$$

where c(x,t) is the concentration of the active agent within the tubule at position x and time t, D is the effective one-dimensional diffusion constant (determined experimentally), and L is the tubule length. In this context, the term "essentially equal length" means that the tubules are prepared using a technique known or intended to produce a. If the active agent is uniformly distributed inside the cylinder at the beginning of the release process, the initial condition is $c(x,0)=c_0$, where $c_0$ is the initial linear concentration of the active agent. Integrating over x gives the total concentration inside the tubule. The concentration released into solution is therefore:

$$c_{solution}(t) = c_0 L - \sum_{n=0}^{\infty} \frac{8c_0 L}{(2n+1)^2\pi^2} \exp\left(-\frac{(2n+1)^2\pi^2 Dt}{L^2}\right)$$

For long times, the release decays as a single exponential with the exponential decay time $\tau(L)=L^2/\pi^2 D$. This long term behavior is the more significant regime for most controlled release applications.

In many (if not most) cases, the tubule population will not be monodisperse. As noted above, unless steps are taken to keep the tubules monodisperse, or unless the tubules are sturdy enough to resist breakage under ordinary handling conditions, tubule populations will tend to the distribution given by:

$$\rho(L) = \frac{1}{L_0} \exp\left(-\frac{L}{L_0}\right)$$

The wider distribution of tubule lengths changes the profile of release as a function of time. For short times, the release is dominated by the shorter tubules, since they are the most common. For longer times, the short tubules become depleted, and the release is dominated by the rarer longer tubules that are still releasing. This crossover can be modelled by integrating over the length distribution to obtain:

$$c_{solution}(t) = c_0 L_0 - \int_0^\infty dL \frac{1}{L_0} \exp\left(-\frac{L}{L_0}\right) \sum_{n=0}^\infty \frac{8 c_0 L}{(2n+1)^2 \pi^2} \exp\left(-\frac{(2n+1)^2 \pi^2 Dt}{L^2}\right)$$

For long times, this release decays not as an exponential but as the stretched exponential $\exp(-(t/\tau(L_0))^{1/3})$. Because this stretched exponential decays very slowly, the release is more linear than a standard exponential decay. Thus, the polydispersity in tubule lengths may be an advantage for release applications.

Preparation of Tubule Batches with Preselected Length Distributions

For the foregoing mathematical models of the effect of length distribution on release rate to be of use to a skilled practitioner, it is necessary for a skilled practitioner to be able to prepare batches of tubules loaded with active agent (and optionally a carrier) for use in a controlled delivery system, where these tubule batches have a preselected length distribution. Lipid tubule batches may be prepared with preselected length distributions by selecting a cooling rate to provide the desired average length. See Thomas et al., "Lipid Tubule Self-Assembly: Length Dependence on Cooling Rate Through a First-Order Phase Transition", Science 267 1635–38 (Mar. 17, 1995), incorporated by reference herein in its entirety for all purposes. With these unfilled tubules of preselected length distribution, it is possible to prepare tubules filled with active agent (and optionally carrier), by standardizing the techniques used to fill the tubules. Techniques have been developed to further aid in the control of tubule length distribution. To reduce the overall length of the tubules one may add a solution of a divalent cation to a suspension of tubules in water. This produces tubules in which the interbilayer distance is increased and the overall length reduced by a factor of 50% or more (depending on the amount of cation added).

Providing Tubules with Degradable Endcaps

By providing tubules loaded with active agent, where some or all of the tubules have one or more types of degradable endcaps, additional advantages may be secured. One advantage is that the endcaps may be selected to remain stable in a storage environment and degrade in the use environment. Thus, the tubules become "smart" tubules, releasing active agent only in the use environment.

Since all endcaps will degrade under some conditions, what is meant by "degradable endcaps" in this context are endcaps that will degrade from a condition that does not permit effective release of an entrapped active agent to a condition that will permit effective release of an active agent. Typically, this degradation takes place upon exposure to a stimulant that will not degrade (or alternatively, will not degrade to the same extent) the tubule. Typically, this degradation takes place after a period of time that is shorter than (or not longer than) a time required to degrade the tubule, i.e., the lifetime of the tubule.

For example, endcaps of polymerizable lipids may be prepared, where the lipid has the formula where n is 1 to 10 and m is 15–n, and where each R is individually selected from the group consisting of dienyl, allyl, methacrylate, dienoate, and mixtures of such moieties, so that these endcaps degrade upon exposure to a stimulant (e.g., water, pH, ion, temperature, light) in the use environment. For instance, endcaps of this material will quickly hydrolyze in pH of about 6.9 or higher. Water will hydrate the headgroups of the lipid, causing channels to open in the lipid bilayer. Likewise, $OH^-$ ions will replace amine headgroup moieties, disrupting the lipid bilayer. Thus, water will act as a stimulant for endcaps of this material. Likewise, diazobenzene groups in these lipids will isomerize in the presence of light, causing channels to open in the lipid bilayer. Likewise, many metal ions will bind to headgroups, to form clusters. These clusters will also disrupt the lipid bilayer, creating channels through the bilayer. See generally U.S. Pat. No. 5,366,881, issued Nov. 22, 1994 to Singh et al. and U.S. Pat. No. 5,290,960, issued Mar. 1, 1994 to Singh, incorporated by reference herein, in their entireties, for all purposes.

Another advantage of degradable endcaps is that since a population of tubules may be prepared with fractions of the tubules having endcaps of various thicknesses, the release profile of the tubule population may be modified, so that fractions of tubules within the population begin to release active agent at various times. For example, 100 Å of copper will degrade in seawater in about one year. Accordingly, a population of tubules could be prepared, where some of the tubules have no copper endcaps, some of the tubules have 100 Å copper endcaps, some of the tubules have 200 Å endcaps, and some of the tubules have 300 Å endcaps. In such a population, the tubules with no copper endcaps would begin to release active agent almost immediately, tubules with 100 Å copper endcaps would begin to release active agent after about one year, tubules with 200 Å copper endcaps would begin to release active agent after about two years, and tubules with 300 Å copper endcaps would begin to release active agent after about three years. Thus, controlled release for periods of over three years may be achieved, with rational control over the active agent release profile.

Figure 1:
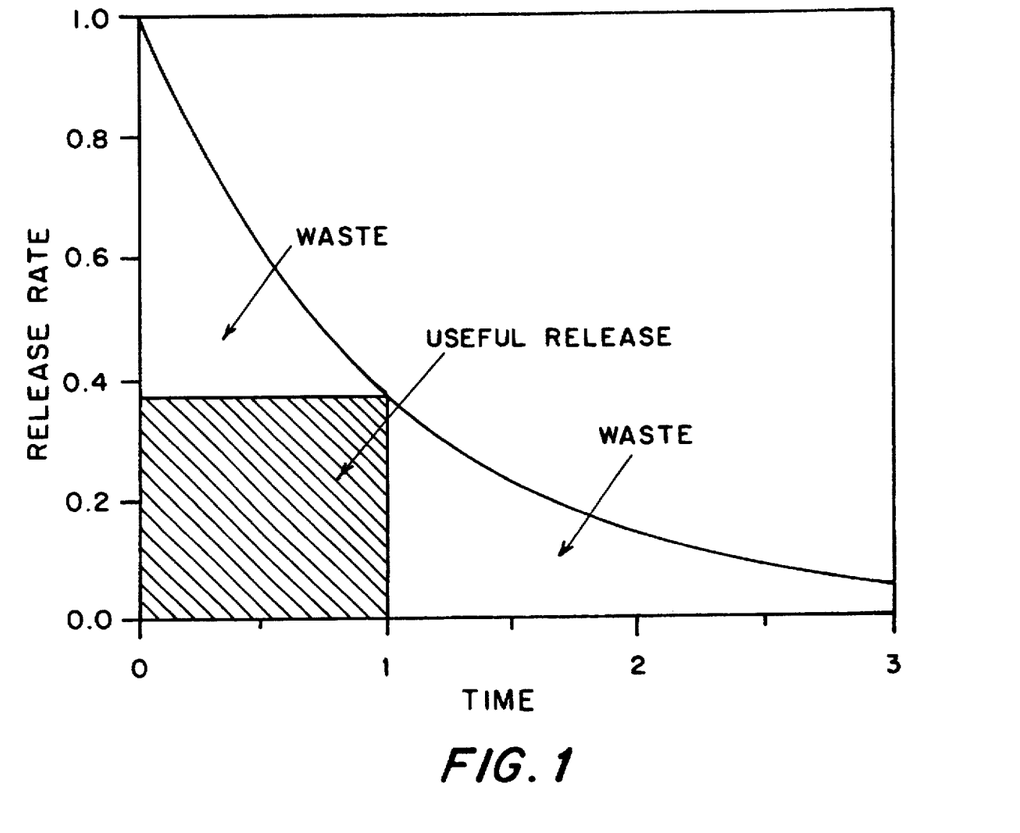
FIG. 1 shows total release and useful release from a tubule population with an exponential release curve, as a function of time.
Figure 2:
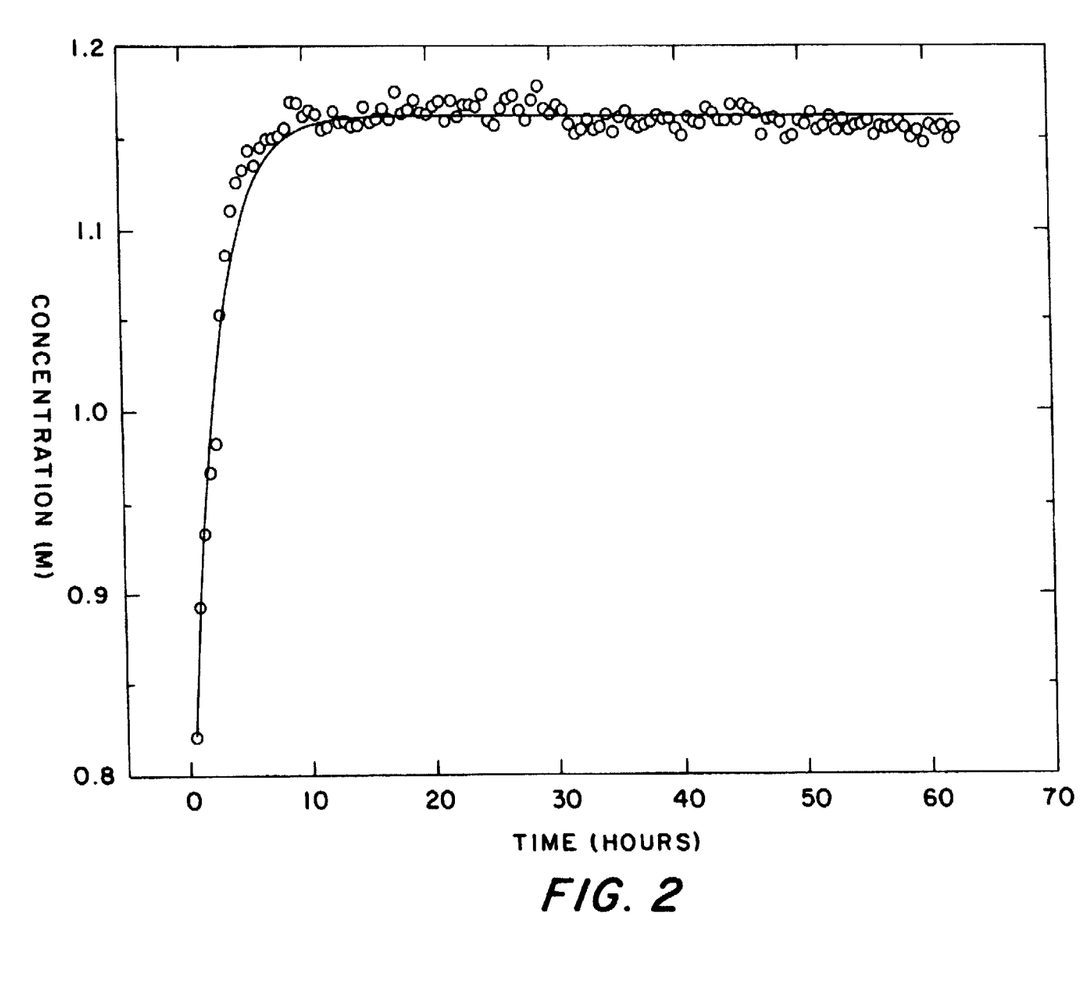
FIG. 2 shows the measured release rate from a monodisperse batch of microcylinders of uniform length.
Figure 3:
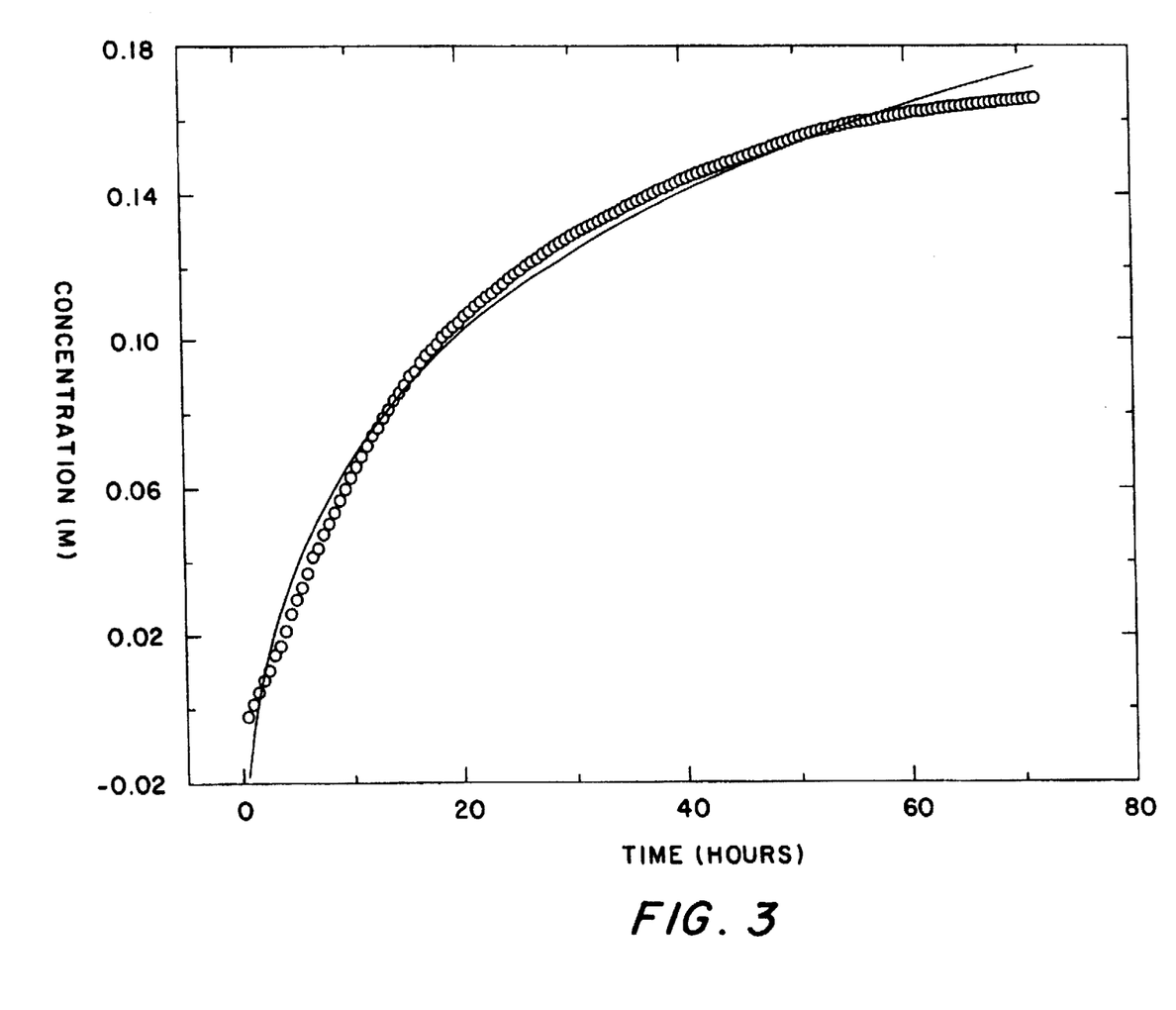
FIG. 3 shows the measured release rate from a polydisperse batch of microcylinders.
Figure 4:
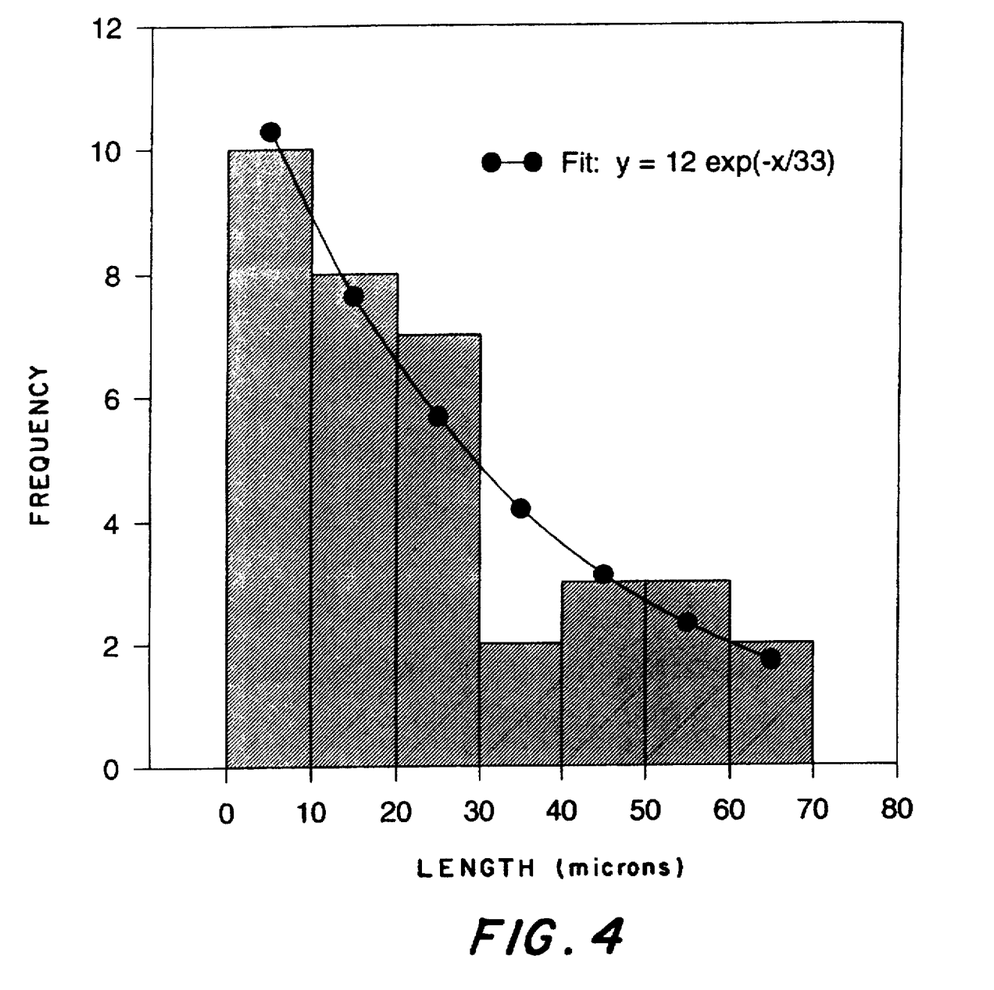
FIG. 4 shows the measured length distribution of a batch of microcylinders.
Figure 5:
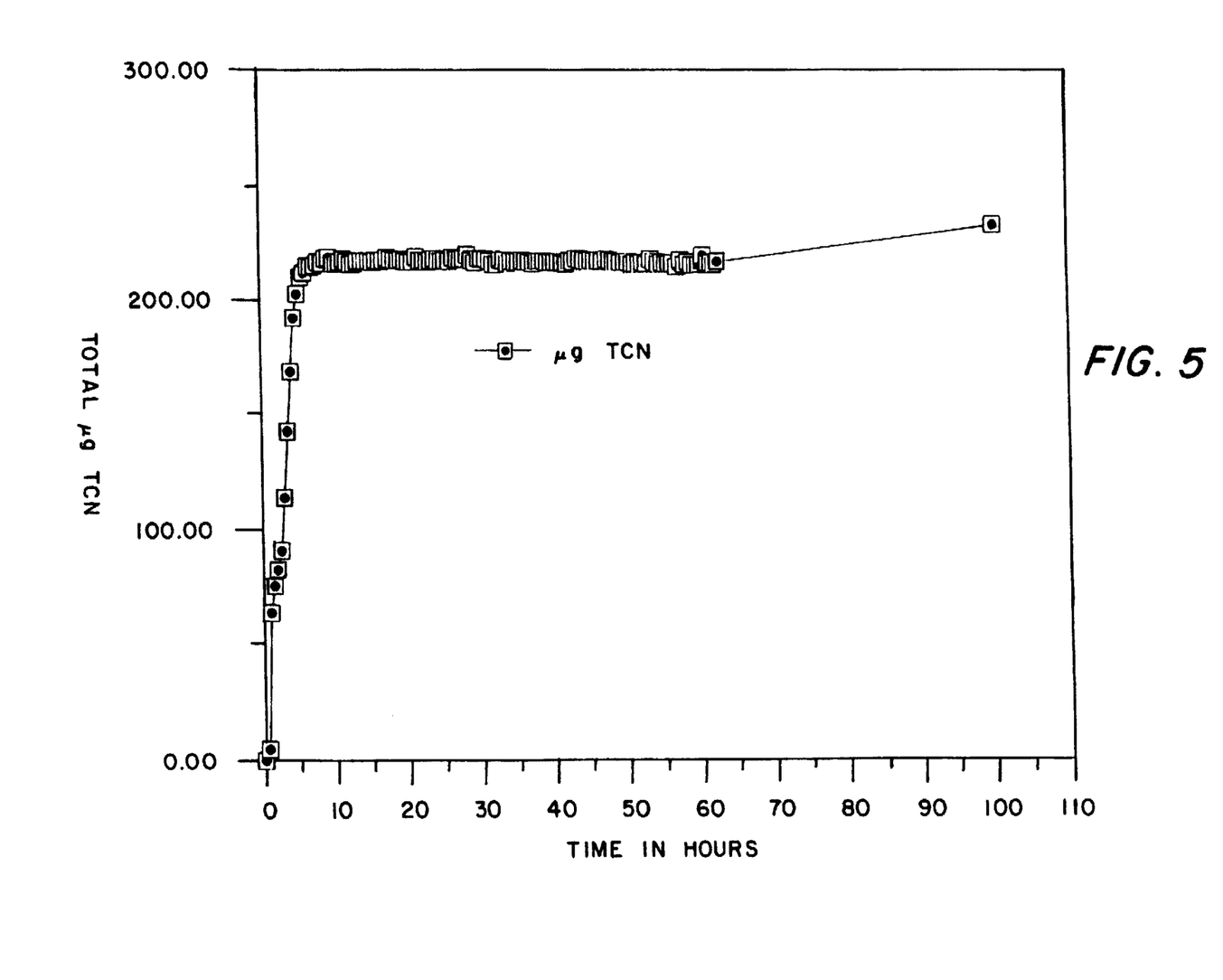
FIG. 5 shows the release of tetracycline from Quietol 651 carrier.
Figure 6:
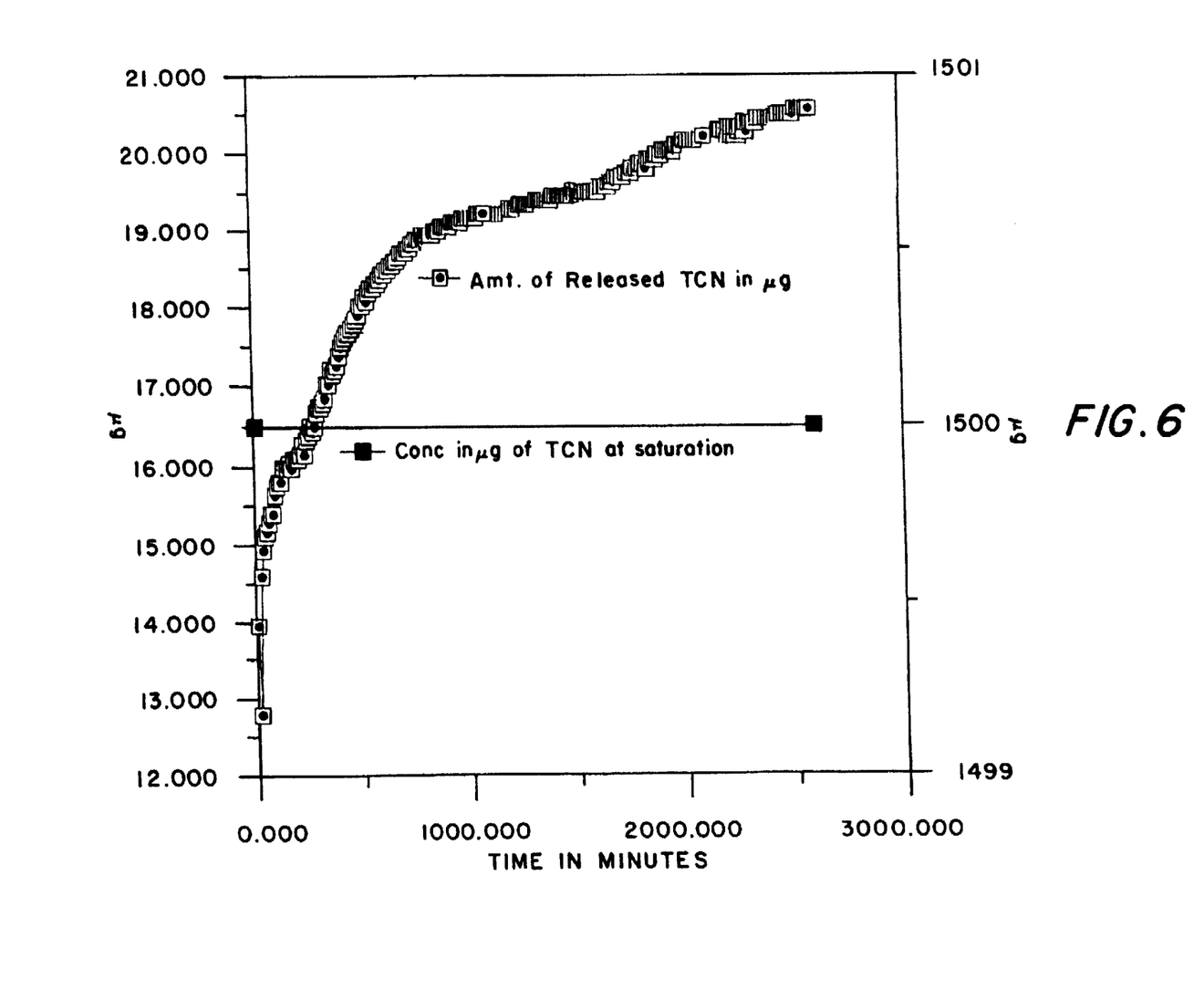
FIG. 6 shows the release profile expressed as the total μg release from a 0.1 g sample of copper tubules in water.
Figure 7:
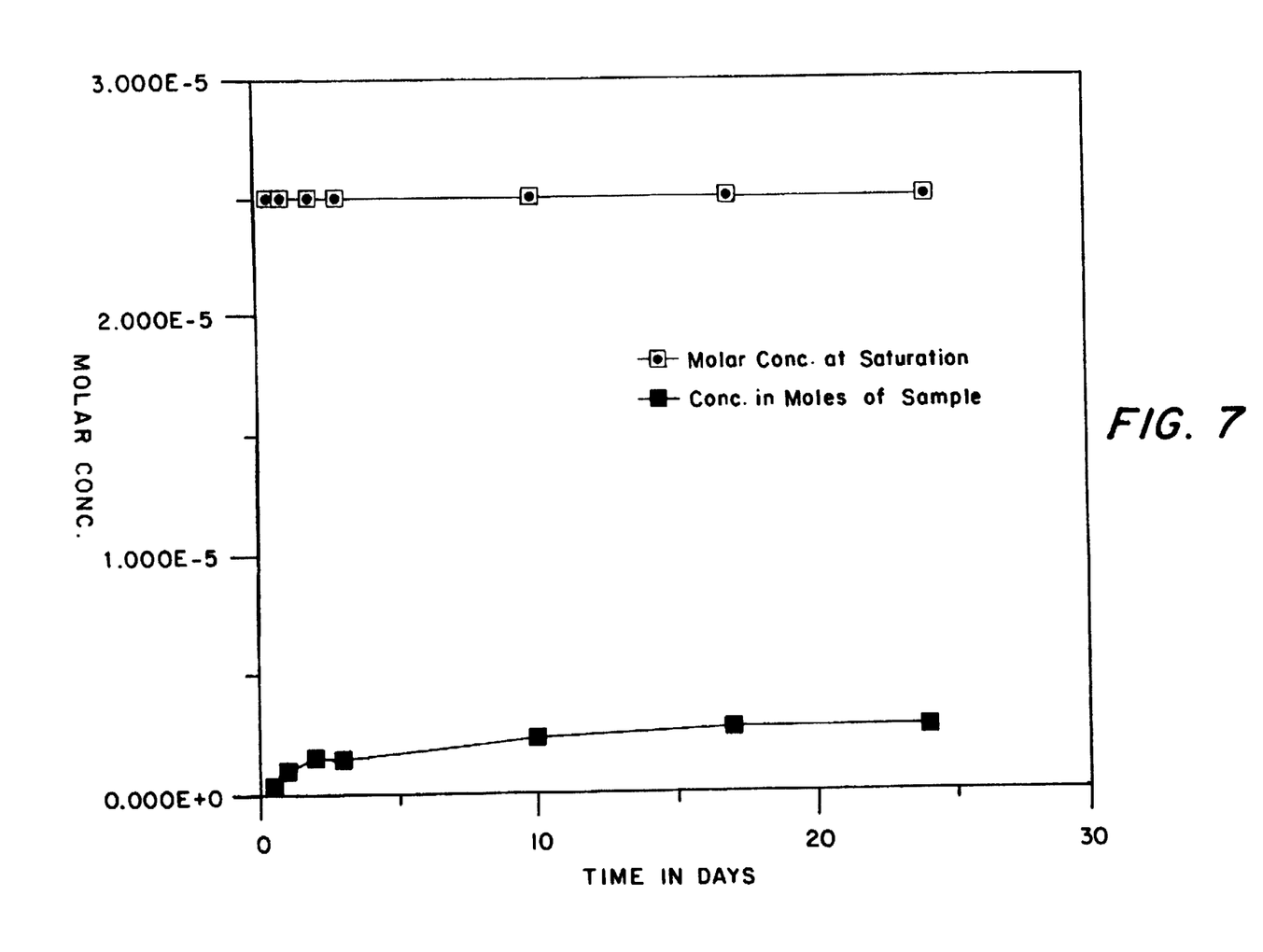
FIG. 7 shows the molar concentration at saturation and the actual molar concentration for FIG. 6.
Figure 8:
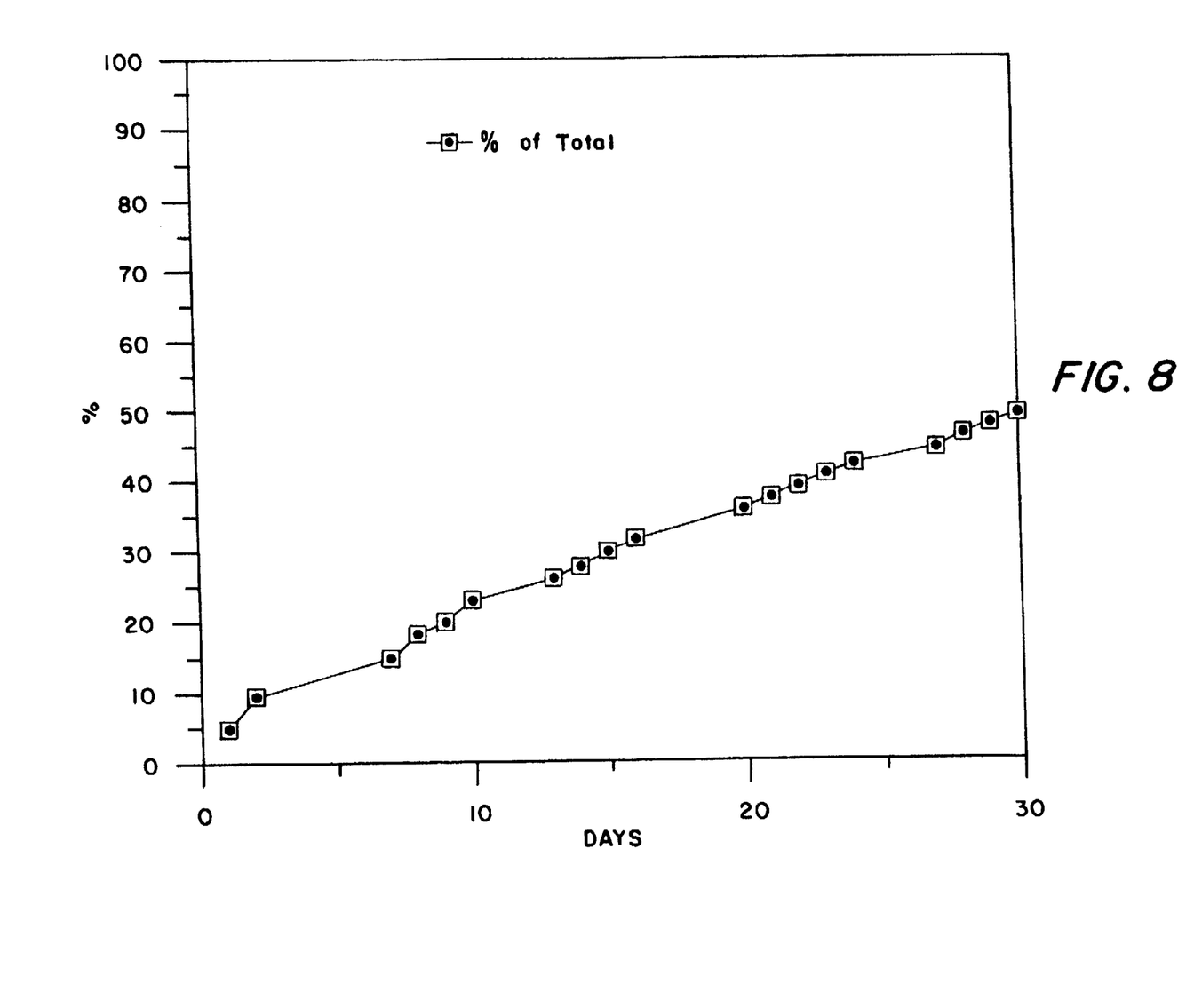
FIG. 8 shows the release profile of tetracycline entrapped in copper tubules which have been suspended in an epoxy resin and coated on a test surface to simulate a paint type coating.

By using degradable endcaps of varying thicknesses, it will be possible to optimize the efficiency ratio ($r_{eff}$ defined as the fraction of active agent released at the target rate) to an extent not possible without the use of endcaps. As shown in FIG. 1, if release rate is plotted as a function of time (shown as approximately exponential here), at early times the release rate is greater than the target release rate. The amount of active agent at the target rate is useful release; the amount above the target is wasted. At later times, the release rate falls below the target rate. The active agent released is also wasted, because it is released at a rate that is too low to have the desired effect. Thus, the efficiency ratio $r_{ef}$ is the ratio of the area in the rectangular region labelled "useful release" to the total are under the release curve.

For a specific example of this efficiency, consider a simple exponential release process, which is given by $$x(t) = a\ \exp(-t/\tau)$$

Assuming the target release rate is a*, for time $t < t^* = \tau$ ln (a/a*) the release rate is greater than the target rate. Thus the useful release is $a^*t^* = (a^*\tau)$ ln (a/a*). By comparison, the total amount of active agent released is $$\int_0^\infty x(t)dt = a\tau.$$

Thus, the efficiency is the ratio of those quantities:

$$r_{ef} = (a^*/a)\ \ln\ (a/a^*)$$

By maximizing this efficiency ratio, it is found that the highest efficiency is achieved if a*/a=1/e≈0.37. Thus, the initial release rate should be about 2.7 times the target rate. The highest value for $r_{ef}$ is 1/e≈0.37. The efficiency does not depend on the release time τ, but it does depend on the shape of the release curve. A differently-shaped release curve would have a different highest value for $r_{ef}$.

Endcaps of varying thicknesses may be produced by various techniques. One such methodology that will vary the thickness for metallic endcaps is to vary the initial bath strength, and the time of plating. By increasing the bath strength, or by increasing the time of exposure to the electroless plating bath the thickness of the metallic coating may be varied. By utilization of a test surface the thickness of metal may be controlled. One would plate a catalyzed surface and then metal coat the surface followed by examination in a scanning electronmicroscope or with a depth profiling apparatus. The thickness elucidated would be the same experienced on the catalytically active ends of the microtubules which were then plated in the same strength of bath for the same time. In the case of an epoxy endcoating the thickness is varied by mixing the catalyst and hardener fraction of the final polymeric mixture into the active agent in the central core of the tubule. The loaded tubules would then be exposed to a solution that contained the agent at saturation and the epoxy non-crossed linked polymer. The tubules would be suspended in the solution and allowed to react. The crosslinking of the epoxy is diffusion dependent and thus the amount of crosslinked epoxy in the cap would be directly proportional to the concentration in the external environment and the length of exposure to the hardener/catalyst leaching from the tubule end. This has resulted in end capping and surface capping of the microtubules and subsequent variation in the release profiles of agent obtained. Another type of cap of various thickness occurs which the agent and a polysaccharide such as sodium alginate of gellan gum a polysaccharide from bacteria is entrapped along with the active agent. When the excess is rinsed from the tubule exterior and the microtubules are suspended in a solution of calcium chloride the calcium chloride immediately reacts with the polysaccharide and cross links the cap. Depending on the length of exposure the thickness of the end cap or plug will be varied. In this example the end cap may be removed by either exposure to an enzyme capable of degrading the polysaccharide or to a potassium containing compound or phosphate containing compound which would then compete for binding sites on the polysaccharide and thus effectively remove the end cap on demand.

Having described the invention, the following examples are given to illustrate specific applications of the invention, including the best mode now known to perform the invention. These specific examples are not intended to limit the scope of the invention described in this application.

EXAMPLE 1

Preparation of a Batch of Lipid Tubules with an Active Agent in the Lumen, Having a Preselected Length Distribution A drug to be entrapped may be dissolved in a suitable alcoholic solvent such as isopropanol, methanol, butanol, or ethanol. The dissolution may be enhanced by heating and sonication. The tubule forming lipid may then be added to the solution at a concentration between 1 mg/ml to 100 mg/ml and the temperature may be raised to about 60° C., and the mixture may then be agitated until all of the lipid has been dissolved. Following this step, the solution may be mixed for a minimum of 15 minutes and then allowed to cool to a temperature between 20° C. and 38° C. at a rate between 0.1° to 1° C./min. This may then be held for a period sufficient to yield tubules.

The microtubules thus obtained may then be removed by filtration or by centrifugation, with the resulting tubules suspended in a solution of sterile water which has been saturated with the drug. Tubules may then be stored at temperatures below their chain melting temperature, which is dependent on the exact lipid used.

Assay for drug loading may be carried out by heating a known weight of tubules in a strong solvent for the drug, which if possible should be a non-solvent for the lipid (example: acetone). Further release rate testing may be accomplished by including drug carrying microcylinders in a solution of water or physiological (isotonic) saline solution which is sufficient to remain unsaturated by the drug, the microtubules may be spun out of suspension at regular intervals and the supernatant may then be analyzed by appropriate methods for drug concentration.

EXAMPLE 2

Preparation of a Batch of Lipid Tubules with Active Agent and Carrier in the Lumen, Having a Preselected Length Distribution Tubules and active agent may be prepared as in the preceding example. However, to increase drug loading further, a suitable carrier may be added to the central lumen of the microtubule as follows. The drug loaded tubules may be added to a small amount of sugar such as trehalose and then freeze dried. Following the freeze drying, a powder consisting of dry lipid tubules will be obtained. The drug may then be sequestered in micelles formed from a phospholipid and then added to a carrier material at the highest possible percentage by weight that may be obtained for the phospholipid/active agent complex. One example of such a carrier would be sodium alginate. In this example the agent would be mixed with sodium alginate. Following this uncrosslinked carrier and drug would be entrapped in the dry microtubules by capillary attraction simply adding the agent/sodium alginate to the tubules and then rinsing the exogenous material from the exterior of the tubule by suspension and filtration. This step should be repeated until the exogenous carrier is removed from the tubules. The tubules/drug/carrier complex then may be added to a dilute solution of calcium chloride, or alternately the use of a sequestrant such as polyphosphate may be mixed with the alginate at a ratio of 0.5% by weight and then the alginate blended with a very small amount of calcium sulphate to set the gel by internal release.

The drug may then be filtered or centrifuged to remove the calcium chloride solution and re-suspended in a saturated sterile water solution, or freeze-dried for storage. Alternate carriers may be methyl cellulose, bacterially derived gums such as gellan gum or gar gum, polylactic acid, polyglycolic acid, chitosan, pva, and pvp.

EXAMPLE 3

Confirmation of Tubule Release Profile

The release rate was measured from a monodisperse batch of microcylinders of uniform length L=10 μm with a polymeric carrier (50/50 mixture Quietol 651/DER 736) by adding the agent containing cylinders to 250 ml of water in a 500 ml beaker and then pumping the supernatant through a flow cell in a Perkin Elmer 6000 uv/vis spectrophotometer and measuring the absorbance of the solution vs. time. The time dependent nature of the release could then be calculated from the absorbance and plotted vs. time until 100% of the entrapped agent was observed to have been released. The data are shown in FIG. 2. The measured release curve gives a good fit to the predicted function, with the release time $\tau(10\ \mu m)\approx 2.4$ hr, and from this fit an effective diffusion constant of $D=4.22\ \mu m^2/hr$. This value of D was used to predict the release from a polydisperse batch of microcylinders with an exponential length distribution, with the average length $L_0=33$ μm, and with the same polymeric carrier. The parameter $\tau(10\ \mu m)$ was constrained to be 2.4 hr, as determined earlier. The data are shown in FIG. 3. The measured release curve agrees with the prediction, with the same value of D. Accordingly, the theory is able to predict the dependence of release period on microcylinder length for this controlled release system.

EXAMPLE 4

Confirmation of Tubule Length Distribution

A batch of polydisperse tubules were prepared as in Example 1. The tubule lengths were measured by utilization of a micrometer eyepiece in a light microscope. The results are shown in FIG. 4.

EXAMPLE 5

Shortening Tubules to a Preselected Length Distribution

A batch of lipid tubules having a preselected mean length in excess of 200 μm were prepared, and the lengths were measured by utilization of a micrometer eyepiece in a light microscope. A solution of a divalent cation was added to a suspension of tubules in water. These tubules were observed to retain lengths not exceeding 80 μm. The cation solution was Calcium chloride at a concentration of 0.2M, the tubules were added to this solution and were observed to become shorter in length due to the charge interaction of the calcium with the phosphocholine headgroups which has the result of changing interbilayer spacing and headgroup packing within the lipid walls of the tubules. The direct result of this was that of disruption of the tubule structure and the subsequent shortening of the length distribution of the remaining tubules. Subsequent processing was identical to non-shortened tubules.

EXAMPLE 6

Release of Tetracycline, using Various Release Methods

The saturation of tetracycline in water is 0.03 g/100 ml. A standard sample size of 50 ml was used throughout. In each case where a carrier was used, Quietol 651 was used as the carrier. Two release methods were used, and are discussed individually below.

Method 1: Tetracycline was added to the carrier at saturation, the carrier was either mixed with a cross-linker and a known weight spread across on a substrate such as a glass slide, or the copper microtubules were weighed and added to a conical test tube with the total computed amount of TCN available calculated to remain under saturation. Water was then circulated through the 50 ml conical tube and then passed though a flow cell for uv/vis absorbance measurements taken at selected time intervals under computer control.

Method 2: Tetracycline in tubules was painted onto either glass slides or glass test rods and then put into a conical test tube filled with 50 ml of water, which was then changed with each measurement. In this case the absorbance was converted from Beer's Law plot data into μg/ml concentration data with the total released from the microtubules calculated.

Method 1 was used for the carrier material and for just the tubules, Method 2 was used for coatings containing the tetracycline in tubules in an epoxy coating.

FIG. 5 shows the release of tetracycline from Quietol 651 carrier epoxy only. Film cast on glass, stripped, and tested for release. This was a portion of the sample that was further entrapped in copper tubules for characterization of release from tubules.

FIG. 6 shows the release profile expressed as the total μg release from a 0.1 g sample of copper tubules in water. This graph expresses the release from tubules only.

FIG. 7 shows the molar concentration at saturation and the actual molar concentration for FIG. 6, as a means of accessing the diffusional pressures during the release experiment.

FIG. 8 shows the release profile of tetracycline entrapped in copper tubules which have been suspended in an epoxy resin and coated on a test surface to simulate a paint type coating. The sample contains 0.1259 g of tetracycline total within the entire sample.

EXAMPLE 7

Release of Khellin, using Various Release Methods

Khellin is a natural extract from the seeds of the Ami visnaga tree, which are used in human medicine as a vasodialator, and which is a narcoleptic agent for barnacle larva. Khellin is an example of a compound that has an activity similar to many coral extracts and which has proven suitable for use in antifouling coatings.

Figure 9:
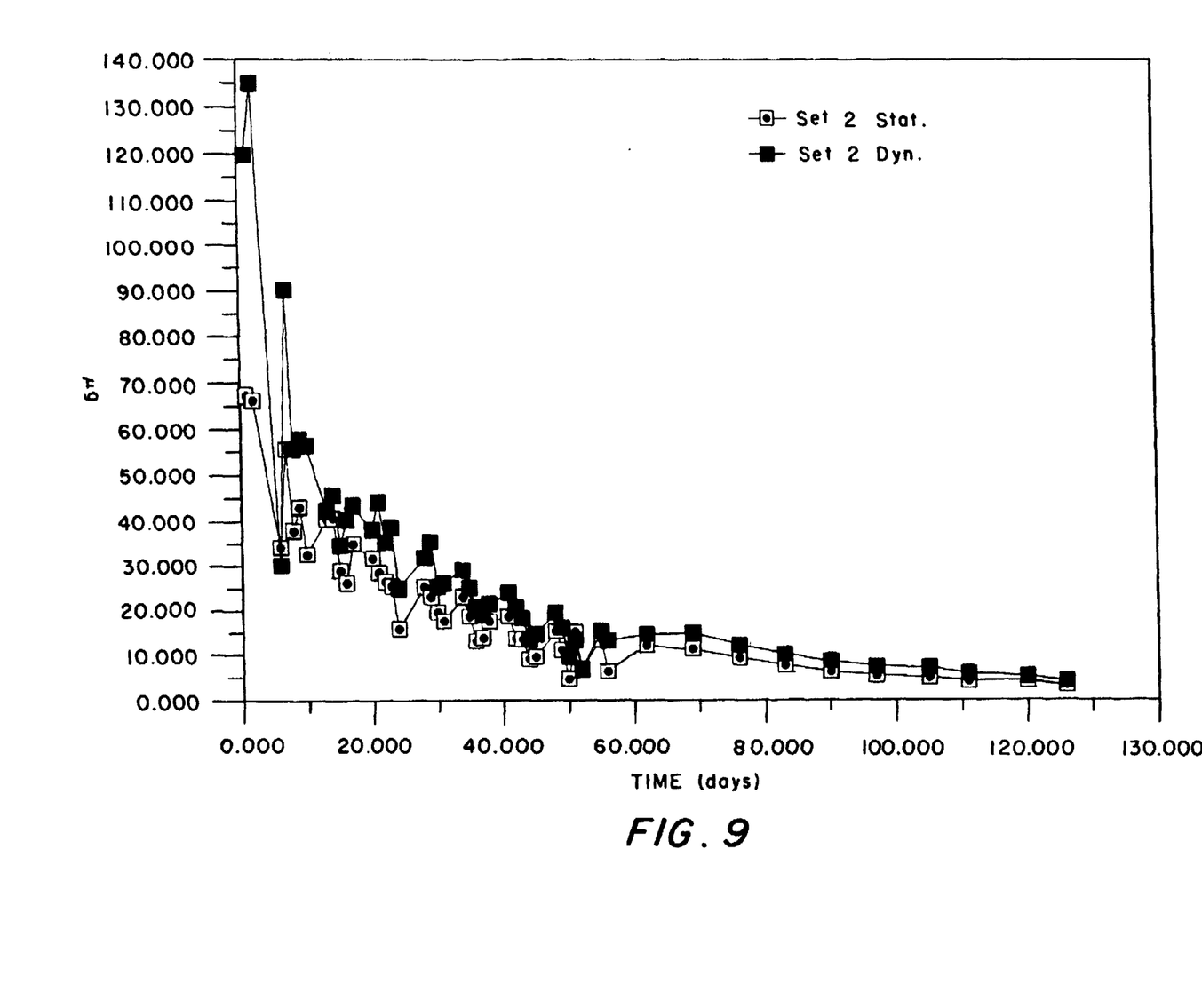
FIG. 9 shows the release of Khellin.

FIG. 9 shows the release of Khellin from ABC#3 coating from DEVOE, which does not contain tubules and which does have tubules added, and also the release from tubules only (illustrating the release profile obtained from just the tubes themselves). Film thickness was 0.425 mm. Loading was 0.6% active agent.

Obviously, many modifications and variations of the present invention are possible in light of the above teachings. It is therefore to be understood that, within the scope of the appended claims, the invention may be practiced otherwise than as specifically described.

What is claimed is:

1. A population of tubules having an active agent contained within the lumen of said tubules, for controllably releasing said active agent from said tubules, wherein said tubules in said population have an average length $L_0$ given by $$L_0 = \sqrt{\tau_f \pi^2 D}$$

wherein $\tau_f$ is the time necessary to release a desired fraction of said active agent from said tubules, and wherein D is the overall diffusivity of said active agent out of said tubules.

2. The population of claim 1, wherein said desired fraction of said active agent is about $1-1/e$.

3. An essentially monodisperse population of tubules of length L having an active agent within the lumen of said tubules, for releasing said active agent from said tubules so that at time t the tubules have released $c_{solution}$ active agent, wherein $$c_{solution}(t) = c_0 L - \sum_{n=0}^{\infty} \frac{8c_0 L}{(2n+1)^2 \pi^2} \exp\left(-\frac{(2n+1)^2 \pi^2 Dt}{L^2}\right)$$

wherein $c_0$ is the initial linear concentration of the active agent within said lumen and wherein D is the effective one-dimensional diffusion constant for said active agent out of said lumen.

4. A population of tubules of mean length $L_0$ and a length distribution $\rho(L)$ approximated by $$\rho(L) = \frac{1}{L_0} \exp\left(-\frac{L}{L_0}\right)$$

wherein said tubules have an active agent within the lumen of said tubules for releasing said active agent from said tubules so that at time t the tubules have released $c_{solution}$ active agent, wherein $$c_{solution}(t) = c_0 L_0 - \int_0^{\infty} dL \frac{1}{L_0} \exp\left(-\frac{L}{L_0}\right) \sum_{n=0}^{\infty} \frac{8c_0 L}{(2n+1)^2 \pi^2} \exp\left(-\frac{(2n+1)^2 \pi^2 Dt}{L^2}\right)$$

wherein $c_0$ is the initial linear concentration of the active agent within said lumen and wherein D is the effective one-dimensional diffusion constant for said active agent out of said lumen.

5. A method for releasing an active agent into a use environment, comprising the steps of:

selecting a release profile for releasing said active agent into said use environment, said preselected release profile having an associated time constant $\tau_f$ for the release of a desired fraction of said active agent;

selecting a population of tubules having average tubule length $L_0$, wherein $L_0$ and $\tau_f$ are related according to the formula $$L_0 = \sqrt{\tau_f \pi^2 D}$$

where D is the overall diffusivity of said active agent out of said tubules;

disposing said active agent within the lumen of said population of tubules; and disposing said population of tubules into said use environment.

6. The population of claim 1, wherein said tubules are nonpermeable to said active agent.

7. The method of claim 5, wherein said desired fraction of said active agent is about $1-1/e$.

8. A method for releasing an active agent into a use environment, comprising the steps of:

selecting a release function $c_{solution}(t)$ for releasing said active agent into said use environment;

selecting an essentially monodisperse population of tubules having tubule length L, wherein $c_{solution}(t)$ and L are related according to the formula $$c_{solution}(t) = c_0 L - \sum_{n=0}^{\infty} \frac{8c_0 L}{(2n+1)^2 \pi^2} \exp\left(-\frac{(2n+1)^2 \pi^2 Dt}{L^2}\right)$$

where D is the effective one-dimensional diffusion constant for said active agent out of said lumen;

disposing said active agent within said lumen of said population of tubules, where $c_0$ is the initial linear concentration of the active agent within the lumen of said tubules; and disposing said population of tubules in said use environment.

9. A method for releasing an active agent into a use environment, comprising the steps of:

selecting a release function $c_{solution}(t)$ for releasing said active agent into said use environment;

selecting a population of tubules of mean length $L_0$ and a length distribution function $\rho(L)$ approximated by $$\rho(L) = \frac{1}{L_0} \exp\left(-\frac{L}{L_0}\right)$$

wherein $c_{solution}(t)$, $L_0$, and L are related according to the formula $$c_{solution}(t) = c_0 L_0 - \int_0^\infty dL \frac{1}{L_0} \exp\left(-\frac{L}{L_0}\right) \sum_{n=0}^\infty \frac{8c_0 L}{(2n+1)^2 \pi^2} \exp\left(-\frac{(2n+1)^2 \pi^2 Dt}{L^2}\right)$$

wherein D is the effective one-dimensional diffusion constant for said active agent out of the lumen of said tubules;

disposing said active agent within said lumen of said population of tubules, where $c_0$ is the initial linear concentration of the active agent within the lumen of said tubules; and disposing said population of tubules in said use environment.

* * * * *